United States Patent [19]
Guthrie et al.

[11] Patent Number: 5,230,623
[45] Date of Patent: Jul. 27, 1993

[54] OPERATING POINTER WITH INTERACTIVE COMPUTERGRAPHICS

[75] Inventors: Barton L. Guthrie, Arlington, Va.; Eric R. Cosman, Belmont, Mass.

[73] Assignee: Radionics, Inc., Burlington, Mass.

[21] Appl. No.: 805,371

[22] Filed: Dec. 10, 1991

[51] Int. Cl.$^5$ .............................................. A61C 19/04
[52] U.S. Cl. ...................................... 433/72; 433/75; 128/774; 128/777; 33/513; 340/710
[58] Field of Search .................... 433/72, 75; 128/774, 128/776, 777, 778; 33/513, 514; 340/710

[56] References Cited

U.S. PATENT DOCUMENTS

| | | | |
|---|---|---|---|
| 4,447,207 | 5/1984 | Kataoka et al. | 128/777 |
| 4,575,805 | 3/1986 | Moermann et al. | 128/776 |
| 4,760,851 | 8/1988 | Fraser et al. | 128/774 |
| 4,788,987 | 12/1988 | Nickel | 128/777 |
| 4,922,236 | 5/1990 | Heady | 340/710 |
| 4,997,369 | 3/1991 | Shafir | 433/72 |
| 5,082,001 | 1/1992 | Vannier et al. | 128/774 |

Primary Examiner—John J. Wilson
Attorney, Agent, or Firm—Richard J. Birch

[57] ABSTRACT

This invention relates to any operating pointer or arm apparatus whose position can be detected and read out on a computer and associated graphics display, and where the pointer can be changed from its pointer function to a "3D mouse" so as to alternately by use control the functionality of the computer as in calibration and display features. Specific embodiments of the invention are given, and one of them is a neurosurgical operating arm which has electronic readout for coupling to a computergraphic display which shows the position of the arm relative to patient anatomy. In one embodiment, the arm has five angular degrees of freedom to achieve a pointer position anywhere in space, at any angle. Electronic readout from the arm positions and joint angles are assimilated into a computegraphic display system. The display system displays anatomical image data taken from the patient with modern imaging techniques. Calibration steps are described to relate the initialization and the patient-related calibrations of the operating arm during surgery. A manual or footswitch control changes the operating arm from a space pointer to a "3D Mouse" that enables easy surgeon interaction with the computergraphics and control thereof. A unique arm geometry is described with specific joint and linkage configurations. In addition, a means for skin or skull-based fiducial system or a bite or dental impression-based frame with localizer rods for providing fiducial points is described for intraoperative calibration of the arm relative to the patient's anatomy. Other embodiments of pointers involving optical or ultrasonic detection are given as examples.

18 Claims, 3 Drawing Sheets

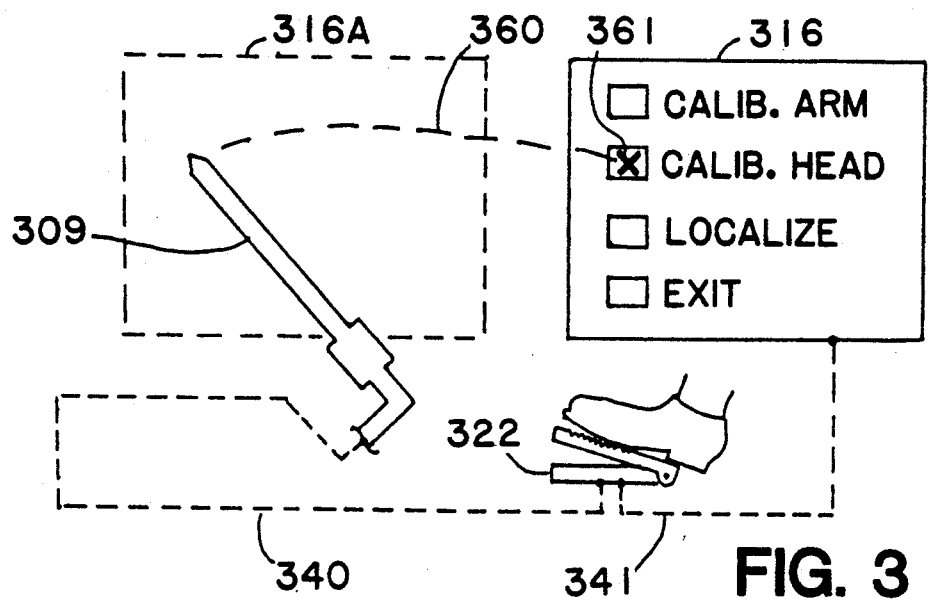
FIG. 3
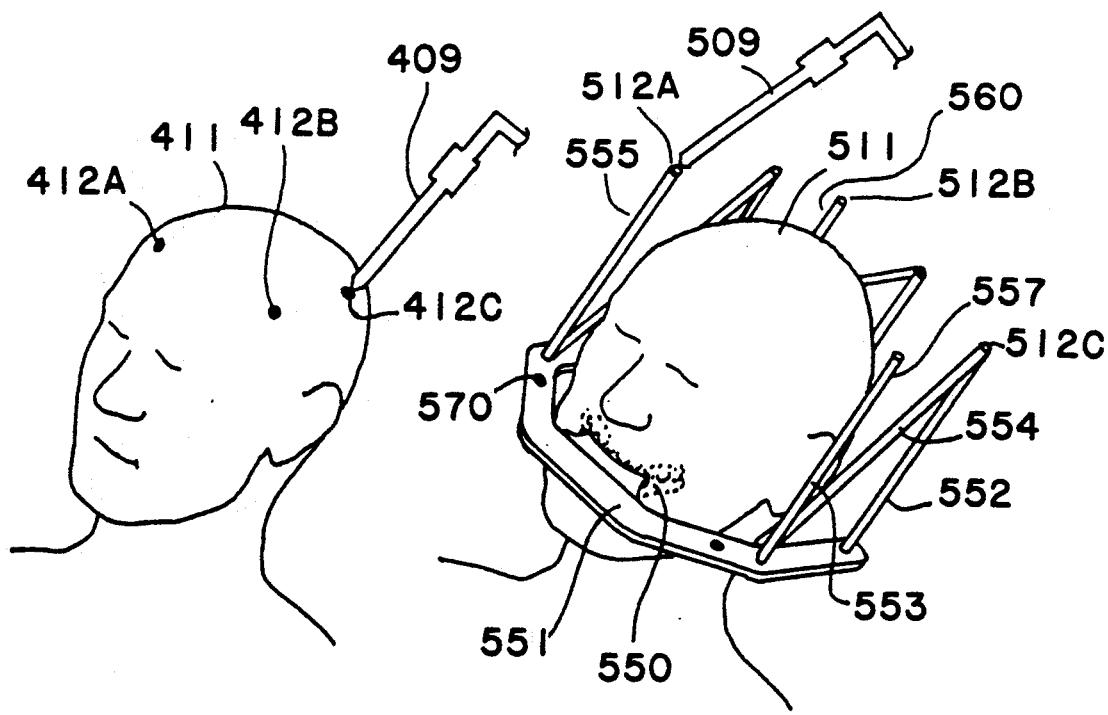
FIG. 4
FIG. 5

OPERATING POINTER WITH INTERACTIVE COMPUTERGRAPHICS

BACKGROUND TO THE INVENTION

The field of human stereotactic neurosurgery is over 40 years old. Stereotactic neurosurgery has usually involved the attachment of a frame to the patient's skull. Various imaging method are used to relate the position of the frame to the patient's anatomy. Thereafter, that data is used to guide the operative approach to a desired target which is seen on the image data. The target, which represents a physical point in the patient's head, may be pre-calculated in a variety of ways depending on the image data. Its known three-dimensional coordinates relative to the stereotactic frame can be further determined, and typically a mechanical arc system fastened to the patient-attached frame is used to stabilize and guide a probe to a target. This technique is widely known in neurosurgery and represents one of the fundamental techniques in that field.

More recently, attempts have been made to eliminate the need for a frame that is attached rigidly to the patient's skull. Thus, the field of "frameless stereotaxy" has become very active in the past year. Several investigators have made attempts at a frameless stereotactic mechanical arm as well as a frameless, non-mechanically coupled system to determine the position of a probe relative to the patient's anatomy without the need for a head frame. Most notable is the work by the present author, Dr. Barton Guthrie, who for many years has worked on an evolution of operating arms for the purpose. Other persons and organizations who have made similar operating arms following the lead of Dr. Guthrie are Dr. Maciunas, Dr. Watanabe, the ISG Company of Canada, and Dr. Reinhardt of Switzerland. In each of the latter four cases, the investigators have used an operating arm with six angular degrees of freedom. What is meant by this is an arm with articulating joints that gives rise to angular movements of arm linkages. One of the authors, Eric Cosman, has also investigated the use of optical coupling to determine a pointer's or probe's position, rather than mechanical coupling.

Dr. Guthrie has evolved an operating arm over the past several years in experimental and pre-clinical release investigations. In some embodiments, he has used five articulating joints, although six or more could also be used. Mathematically, five articulating joints are sufficient to place a pointer at a give position in space from a arbitrary angular direction. This statement is moderated only by the fact that real mechanical operating arms have certain joint and linkage limits which in turn limit the positional and angular approach range of the device. However, within this operating range of the device, five degrees of freedom are sufficient. Thus, one of the embodiments of the development of Guthrie has involved one less degree of freedom than all other investigators have incorporated in their systems and separates the author's invention from all other such devices that have been conceived to date. The use of more degrees of freedom increases the overall flexibility of the operating arm. It also can increase in some situations the operating range, both in position and in angular orientation of a probe. This would be a further positive aspect of using six or more degrees of freedom. However, the more degrees of freedom one uses, the more complex the apparatus becomes and thus the more difficult it is to maintain accuracy. With the proper configuring of five degrees of freedom, the present invention enables wide flexibility of approach and position while maintaining an intrinsic simplicity that all other such devices do not have. The stability and accuracy of the present invention is reflected in this simpler construction with fewer degrees of freedom. Specific arrangements of the five degrees of freedom of the present invention make it practical and functionally easy to use. Avoidance of so-called "gimble-lock" is achieved only by proper configuration of the joints and the links in an operating arm. This has also been achieved in the present invention with a unique geometric configuration. We have also developed unique six degree of freedom arms, and they will be described below as part of this information.

Other types of operating arms or pointers have been developed using ultrasonic and optical detection means to determine the pointers's position. These too may be considered "frameless" devices, although in all cases, they can be used with a stereotactic frame as well. What all other investigators have lacked in their devices is a simple way for the operator of the arm or pointer to convert it to a "3D mouse" so that the pointer itself can be used to change the functionality of the computer graphic system, that displays or reads out the pointer's position.

Thus one main objective of the present invention is to have the operating pointer arm, no matter what is operating principle may be, serve alternatively as a space pointer and at another instance a "3-D mouse" for interactive graphic control of the arm itself. This was achieved by switching the operation of the arm from its primary use as a pointer to its secondary use as a mouse for the screen graphics. The switching can be done in a variety of ways: footswitch, hand switch, third-party-operated switch, or by the position itself of the pointer in space. This greatly increases the convenience of the system and the facility of its use in a practical setting.

Yet a further objective of the present invention is to provide fiducial point means for calibrating the operating pointer or arm that involves a bite piece, or dental impression piece, that can be attached to the patient's dentition and which included localizer points, rods, or other structures to calibrate the position of the arm relative to the anatomy. In the operating setting, this will enable a skull-referenced fiducial marker system that can be accessed quickly and easily by the surgeon to recalibrate the position of his operating arm relative to the graphic anatomy which is displayed on the video monitor.

Yet another objective of the present invention is to provide novel joint and link configurations, both five and six degrees of freedom, to achieve superior operating flexibility of the arm in use.

DESCRIPTION OF THE FIGURES

FIG. 3 shows a schematic diagram of how the operating arm can be converted to a 3-D mouse by means of a switching system.

FIG. 4 shows the calibration of the operating arm using fiducial points that are located on the patient's anatomy.

FIG. 5 shows a bite piece or dental impression tray based device with localizer rods and points attached to it which can be used as a skull-based calibration system for the operating arm during surgery.

DESCRIPTION OF THE INVENTION

Figure 1:
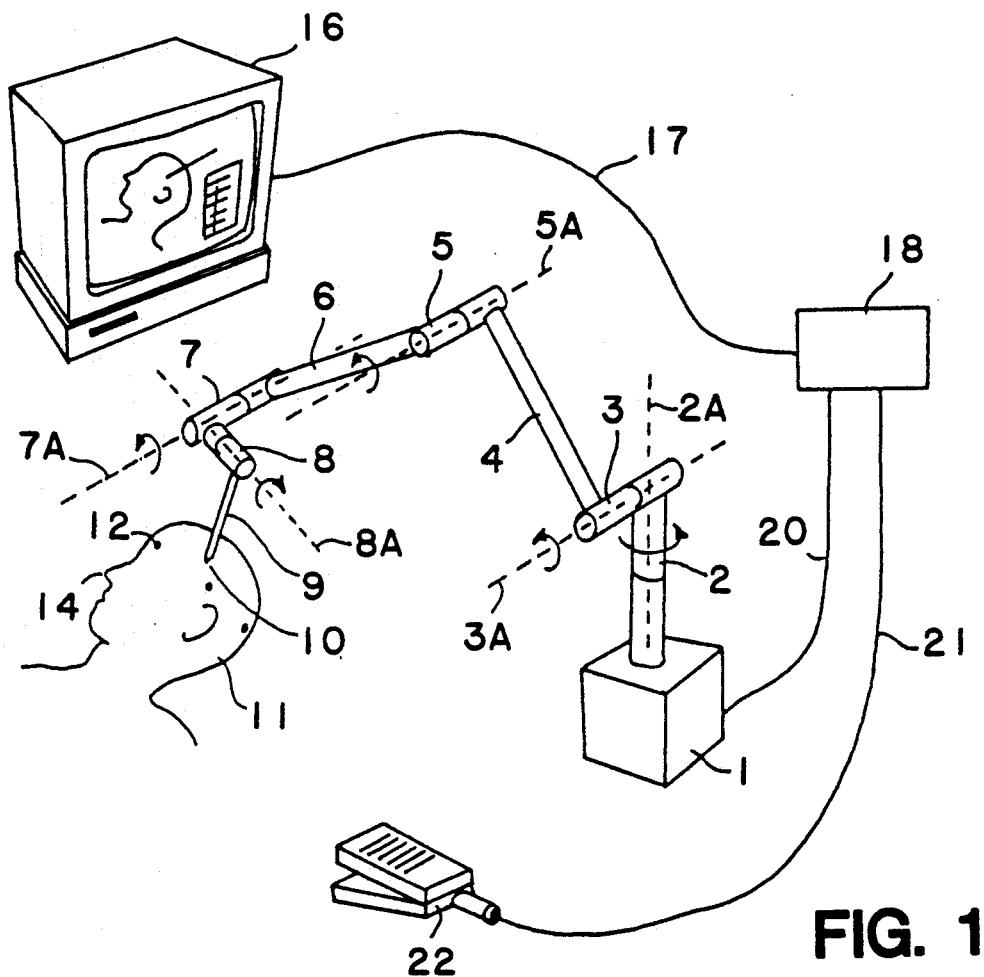
FIG. 1 shows a global view of the mechanical operating arm, together with the graphic monitor and a footswitch means to convert the arm from a space pointer to a 3-D mouse.

Referring to FIG. 1, one embodiment of the present invention is illustrated with a mechanical operating arm. The patient which is being operated on is shown together with the operating aram, a computer-graphic monitor screen, an interface box, and a footswitch system. The arm consists of a base 1 which anchors the arm relative to the patient's head. The first rotation joint is comprised of a vertical element that has a rotating section 2 that rotates about the axis 2A. This in turn attached to a structure which has a rotating element 3 that enables rotation about axis 3A. Axis 3A is perpendicular to axis 2A. Attached to element 3 is the first arm link 4 which is connected to a third joint that has a rotation axis 5A and the rotating element 5 associated with it. Element 5 is connected further to the second arm link 6. This in turn attached to the fourth joint which is associated with axis 7A and rotating element 7. 7A is parallel to 5A, which is also parallel to axis 3A. Element 7 rotates around axis 7A, and it connects to a further joint element which has rotating piece 8 that rotates coaxially with axis 8A. This is the fifth and final axis and rotating joint. Attached to element 8 is the surgical point or operating point 9. This is indicated generically in this figure. It could be a detachable element and have a variety of functions as discussed below. The end point 10 of pointer 9 is designed to point at or touch various portions of the patient's anatomy. In this context, the operating arm is schematically shown relative to a patient's head 11. On the patient's head are index marks, one of which is indicated by point 12, which give fiducial positions that are known relative to an image scan. They can be located physically by the operating pointer 9 during the surgical procedure so as to relate the physical anatomy and the pointer to the patient's anatomy as visualized on the computer graphics. Other natural fiducial points, such as the tip of the noise 14 or structures around the ears and eyes, could obviously be used as natural anatomical landmarks that can be used to calibrate the operating arm relative to the anatomy in a similar way. Also shown is the computer system 16 with its graphic monitor. The computer may have stored in it previously gathered image data of the patient. This data can be brought up and visualized on the computer screen, and the screen may also show a representation of the graphic arm or of the arm pointer 9 as it approaches the physical anatomy of the patient. In this way the surgeon can visually determine where the pointer of the arm is relative to anatomy as represented by the image data. This can be made quantitative as well, showing measurements of distance, accurate relative positions to anatomy, etc. The computer and graphics display may be controlled by controller box 18 which, in turn, is attached to a switching means 22 by cable 21. The connection cable 17 links the controller and the computer. In addition, cable 20 indicates schematically the link from the operating arm to the controller box 18 and thus, in turn, to the computer 16. Controller box 18 may be integral with the computer 16. The electronic detection system in each of the articulating arm joints of arm 8 may be fed into the computer in this way giving a graphic electronic representation of the position of the operating arm on the screen of computer 16. These detectors may be encoders or other positional detection devices.

The switch 22 is indicated as a foot switch, but it equally well could be integral with pointer 9 or a separate switch system altogether operated by a third person. The concept of including the switch 22 with the operating arm is to allow the surgeon himself, by pushing the footswitch, to change the mode of the operating arm from an operating pointer to a digital 3-D mouse or to "click onto" or activate menu functions on the graphics screen. This is described in detail below, but in brief, this enables that the arm itself can be manipulated by the surgeon in the 3-D mouse mode so that he can manipulate to objects, icons, or menus on a computer screen so as to change the function of the arm as in calibration, mode selection and so on.

Figure 2:
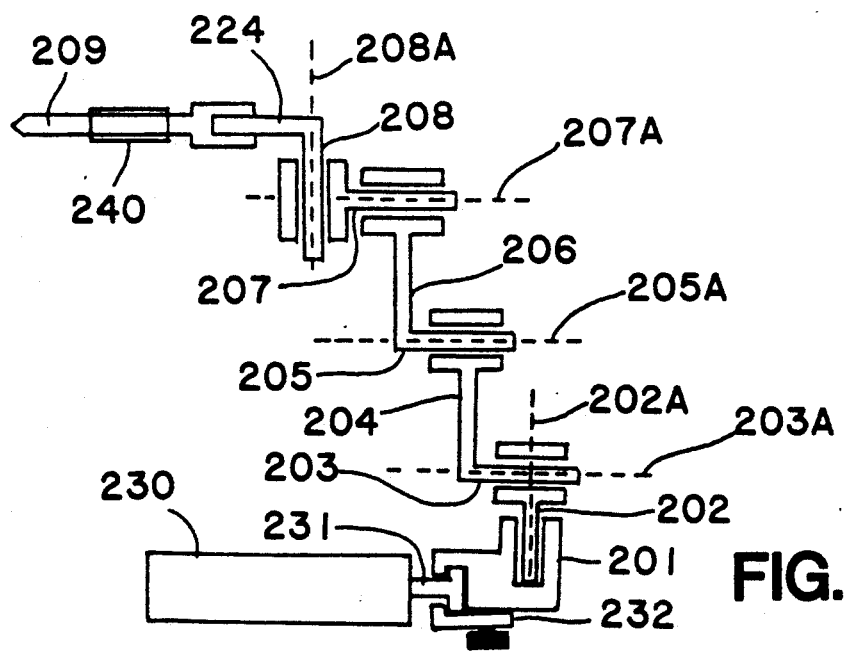
FIG. 2 shows a schematic diagram of the five joint articulating operating arm of the present invention.

Referring to FIG. 2, this shows schematically the five-joint articulating operating arm, which is one of the novel embodiments of the present invention. The base element 201 may be attached via the clamp 232 to a solid platform in the room such as the operating table 230 with its side rail brackets 231. The position of base 201 may be reoriented or moved and reclamped onto the element 231 or any other such element. 201 may actually consist of a pole or bar which can be discretely reoriented in space or translated to discrete positions or moved continuously for the convenience of positioning by the surgeon. Once in position, 201 acts as a stable base for the rest of the operating arm. Element 202 represents the rotating element of the first joint. This rotates coaxially with axis 202A, which may be essentially vertical. The second joint consists of rotating element 203 which rotates coaxially with the axis 203A. This axis is perpendicular to the first axis 202A and is represented here as a horizontal axis. The first arm link 204 connects to the third joint which has a movable piece 205 that rotates coaxially with axis 205A. In this embodiment, axis 205A is parallel to the first axis 203A. Element 205 connects to the second arm link 206 which in turn connects to the fourth rotating joint having the rotating element 207. Element 207 rotates coaxially with the fourth axis 207A. Axis 207A is parallel to axis 205A and axis 203A. The fifth joint contains rotating element 208 which rotates about axis 208A. Axis 208A is perpendicular to 207A. Element 208 is connected to an adaption means schematically indicated as 224. This does not need to be perpendicular to 208, although is shown roughly so in this figure. Element 224 is adapted to join to a probe means 209. Probe means 209 may be a pointer, a stimulating probe, a lesion probe, an ultrasonic probe, or any other surgical apparatus which comes into proximity to the anatomical targets. Although the full scope of the present invention is not limited to a five-joint arm, the embodiment of FIG. 5 with five joints is novel and new and has certain advantages over other operating arms with more than 5 joints. The joint sequences in FIG. 1 are: two joints at the base, followed by a link, followed by a single joint, followed by another link and followed by two perpendicular joints. This 2-1-2 geometry works very effectively. Having the second, third and fourth joints parallel, as shown, also works very well and may be considered as one of several preferred embodiments. Obviously, other choices of joint axes, configurations and orderings such as 2-2-1 configurations are possible and also practical. There are several other novel features of the device shown in FIG. 2. The clamping mechanism to the side of the operating table may be a standard clamp configuration used in the operating setting. In this way the arm can easily be attached to standard tables in a rigid fashion. That is a novel feature which is new with the present invention concepts. The removable tip 209 which can be fixed relative to element 224 is also a unique aspect of the present invention concepts. This could be a simple pointer as shown in FIG. 2, or it could be a suction device, a bipolar or monopolar forceps or tissue separating forceps, an electromagnetic tissue removal device, and ultrasonic probe, an electrode for stimulating or recording of the brain cortex, a laser light or laser delivery device, an endoscopic visualization device, and any of several other types of surgical probes. For each of these types of applicators, one can determine quantitatively where the tip of the instrument is relative to the anatomy shown on the imaging-based computer graphics, and thus relate the actual physical position of the said tip to physical anatomy at all times during the surgery.

Another feature which we wish to claim in this patent is a locking or clamping mechanism for the articulated arm or similar operating arms of FIG. 1 and 2. The pointer 9 may be directed to a desired point in space, and a secondary physical clamp may be brought into position to hold it in that configuration. Alternatively, the joints themselves may have locking mechanisms so that the entire arm can be locked in a given position so that the surgeon does not need to hold the arm in that position while operating surgically.

Referring to FIG. 3, the toggling or switching feature of the present invention is schematically illustrated. 309 represents the surgical probe or pointer of operating arm. Its position in space is electronically determined and carried by the information carrying element 340 to a switch system 322, in this figure illustrated as a foot switch. The switch could equally well be integrated into the pointer 9 or at some other physical location. The switch has another connection element 341 to the computer and computer graphic module 316. The graphics display of the computer is illustrated here as having various functionality or menu options: calib arm, calib head, localize, and exit. These are merely examples, and many others may be devised. By pressing the switch 322, the arm may be activated as a "3D-Mouse". This means that in the 3D-Mouse mode, the pointer 309 can be moved in space by the surgeon thus tracing out in an imaginary mathematical frame 316A its position as visualized by a cursor or crosshair 361 on the actual graphic screen 316. The dashed line 360 represents this imaginary mathematical correspondence and the cross 361 would indicate the corresponding position of the 3D-Mouse pointer on the actual menu screen 316. Thus by moving the pointer 309 manually, the cursor 361 can be moved around on the actual physical screen 316. It can be pointed to any of the various menu window positions. Pressing the footswitch again thereby activates that menu option. One similarly can switch the mode of the operating arm to the calib arm menu option, in which mode the arm is set into a holster or "home position" in which the relative orientation of the joint angles and links are predefined so as to initialize the geometry and configuration of the arm with respect to the computer. In the calib head mode, the probe 309 can be pointed to various index points on the head such as 12 in FIG. 1 so as to reference the arm in space relative to the physical anatomy. In the localizer mode, when the footswitch is pressed the instrument or pointer 309 becomes a physical pointer or localizer in space and its graphic representation can be seen on the computer screen. In the exit mode the face screen menu may disappear and only the graphics may show. Many other such menus can be thought of which can be toggled in or out by the 3D mouse. The utility of having the operating arm pointer act not only as a pointer, but also as a 3D-mouse is very significant and one of the novel features of the present invention. It frees the surgeon from need for other assistance in the operating room and enables him to rapidly select different options for the arm or to move from calibration to localization quickly. The switch 322 can be a footswitch, a hand or finger activated switch or the probe 309, or a remote switch.

It is also anticipated that the switch may only act to click onto menu items and that the conversion of the operating arm probe 309 to a 3D mouse can be done in other ways. For example, when moving the arm out of the immediate operating field, the software may recognize that it is remote from the operating field and automatically turn it into a 3D mouse, whereby it becomes capable of pointing to icons such as in the Table 316 in FIG. 3. Then pressing the footswitch 322 can click onto any given menu item, such as the 361. Thus, the presence of a switch in the system may have the functional objective of either converting the operating arm pointer to a 3D mouse or triggering on menu objects.

It is also anticipated that the conversion and utilization of the operating arm pointer 309 from an anatomical pointer to a 3D mouse and for menu options may be done without the need for a physical switch altogether. This patent claims the generalized concept of an operating arm space pointer or any other type of space pointer or wand, whether mechanically or non-mechanically coupled to the computer system, converting to a 3D mouse in conjunction with computergraphics in general and does not necessarily need the intermediary of a mechanical switch. For instance, by bringing the pointer 309 out of a given physical region of interest near the patient, this may be detected by the computer, and the pointer may automatically convert itself to a 3D mouse. Thereafter, pointing to the screen when in 3D mouse mode can automatically activate a function on the screen by another physical manipulation of the probe 309, such as a rapid movement inward toward the direction of the screen or some other type of recognizable movement of the probe or simply a time delay. It may also be voice-activated or sound-activated and not require a mechanical switch in the usual sense. Thus, this invention generally seeks the application of an operating arm as either a space pointer or a 3D mouse in conjunction with computergraphics.

Alternatively, the position of the probe or locating instrument may not be continuously monitored by the computer. The surgeon may initiate a request for information from the computer by depressing a foot pedal connected with the computer. Alternative to a foot pedal, a finger switch or other type of switch means can be used. Thus, the surgeon can get a rapid update of his location or orientation by depressing the foot pedal or alternate switch, causing the system to display instrument location on the computergraphic images of the cranium.

The process by which the surgeon interacts with the computer may be called the interface. The interface for such a surgery and planning system is designed to minimize surgeon inconvenience. The entire program is menu driven. One of the unique features is that during the operation the localizer or probe itself can function as either a "mouse" to allow the surgeon to control program flow without contamination or stepping away from the operating field or as a localizer or pointer to inform the surgeon of his location with respect to the cranium. This feature is a novel aspect of the present invention and is not available, nor has it been suggested for use with any other surgical computer-based operating surgical system.

Referring to FIG. 4, an example of a calibration procedure for the arm will be discussed. The index marks discussed above are shown on the patient's head 411. There are four index marks shown in FIG. 4, although there could be more. They are designated by 412A, 412B, and 412C. Three or more points may be used to calibrate the operating arm by putting its electronic readout into calibration with the actual patient anatomy and thus into calibration with the graphic image-based anatomy which is displayed on computer screen 16 in FIG. 1. This can be accomplished by toggling the 3D mouse into calib head mode illustrated in FIG. 3, and sequentially pointing to the three index points, pressing the footswitch each time the pointer of 309 is contacting index points in sequence. Each time the footswitch is pressed, the electronic information from the arm's joints will be passed to the computer and registered there. After indexing all of the three points in this way, the computer then has the mathematical transformation of the electronic joint readouts for three index points to the coordinates of these index points in the image-base data space stored in the computer 16. Presupposed here is that each index point is observable in the image-based data. This same transformation maps all of the other arm positions as it probes the physical anatomy to the image-based anatomy as seen on the computer, so the connection of the arm as a calibrated space pointer is now complete.

Referring to FIG. 5, another method may be used to graphically map the calibration of the operating arm from the physical patient space to the image graphic space. This involves the use of a bite piece 550 which may have an impression of the patient's upper and/or lower teeth in it. The bite piece 550 is attached to a base plate 551 that in turn has a variety of vertical and diagonal rods or index points located on it. For example, the vertical rod 552 and 557 have between them a diagonal rod 554, forming an indexing "N-structure" (has the shape of an "N"). This is similar to that used for frame-based stereotactic surgery involving the BRW Stereotactic System of Radionics, Inc. Similar N-structures may be placed elsewhere around the head. In FIG. 5 three such N-structures are shown which are sufficient to determine mathematically the plane of an image slice when the slice plane cuts through these structures. Such imaging methodology is well known in the Radionics, Inc. literature. The point of FIG. 5 is to illustrate that a skull connection can be made via a bite piece, associated bridge, and localizer elements so that the localizer elements will stand at a given specific orientation relative to the patient's anatomy. If the patient image scans have been made with such a bite piece localizer in place, then all of the image data stored in computer 16 will be referenced relative to such index rod or points. This has a secondary advantage in accumulating the image data in that it confirms the accuracy of the slice to slice information, since this must give the integrity of the rod structure as straight line elements in the computer graphics if the scan planes have been all done in a parallel fashion. If they are not exactly parallel, the anatomical information can be transformed immediately to the index frame coordinate system and corrections for non parallelity can be made.

In the context of the present operating arm, the fiducial point or fiducial structures shown in FIGS. 4 and 5 can be used to calibrate the arm. For example, in FIG. 5, the pointer 509 of the operating arm may be touched on the ends of the rod such as the end points 512A, 512B, 512C of the associated rods 555, 560, and 552. This will establish specific reference points on the structure and thus a reference point or plane relative to the patient anatomy for calibration purposes. Alternatively, there may be no rod or diagonal structures at all, but merely a base 551 attached to the bite piece 550 with index points such as 570 on it. The bite piece 550 may in fact be integral with the base 551 making a very simple bite piece structure which can be removed with ease from the patient's mouth during operations, even if the patient is intubated or if he is sedated. The concept of using the secondary skull-based localizer in FIG. 5 as compared to the patient-based localizer points in FIG. 4 is novel to the present invention. It has the advantage that index points do not have to be put onto the patient's scalp or embedded into the patient's skull, as schematically indicated in FIG. 4. It also means that repeat scanning or repeat operations may be referenced to the same skull-based platform and coordinate system directly. The bite piece structure 550 and 551 may be securely anchored to the patient's upper teeth by means of straps over the patients head and securing mechanisms from the back of the patient's head analogous to the GTL-Gill-Thomas Localizer manufactured by Radionics, Inc. Alternatively, it may be put in and out of the patient's mouth during the course of the surgery if a calibration of the arm by the surgeon is required. Thus the novel feature of combining a non-invasive dental bite piece with localizer structures associated with it together with an operating arm and computer graphics is new to the field of stereotaxy and claimed in the present patent application.

Figure 6:
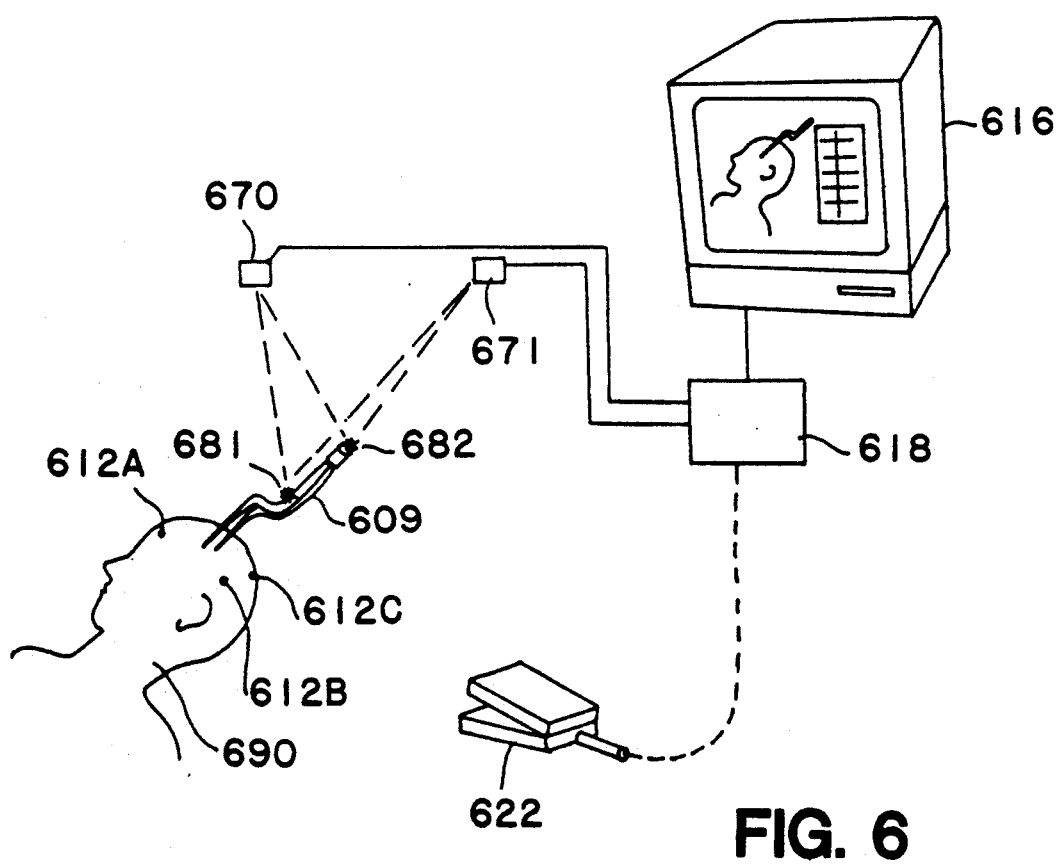
FIG. 6 shows a generic diagram of a surgical pointer, a detector system, and a computer where the surgical pointer can be switched from a pointer mode to a 3D mouse mode.

FIG. 6 shows a more generalized embodiment of the present invention where it is not restricted to a mechanically coupled articulating operating arm. The probe or pointer 609 is now in the form of a bipolar forceps, which is one particular embodiment of such a probe analogous to a standard surgical instrument. On it are index points, as an example 682 and 681, which may be optical or ultrasonic senders or receivers that can be interrogated by sensors or receivers 670 and 671. They in turn go to an interface box 618 which can assimilate the signal and send it on to the computer and graphics display system 616. The exact nature of the interrogation between the points 681 and 682 and the elements 671 and 670 does not have to be specific here. As examples cited above, they could be optical, CCD, or camera sensors. They could be ultrasonic detectors and senders where triangulation of time delays or angular measurements could be present. There are a multiplicity of other types of schemes which can generically give a probe and cooperatively coupled detection or sensing elements analogous to this scheme that can tell the position of the probe relative to such sensing devices. There could be mechanical coupling as an operating arm, or electromagnetic coupling, or sonic coupling. In any case, the position of the probe 609 relative to the patient's anatomy 690 is possible by a variety of physical principles, as illustrated in the FIGS. 1-6. The graphics representation in computer display 616, together with the graphics representation of both the anatomy and the probe position is as described above. A mechanical switch, such as 622, might be present or the switching may be done by software means and other principles as described previously. FIG. 6 thus illustrates the generalized concept of a probe, cooperative sensing means coupled to a computergraphics system, and a generic switching means so that the probe can be switched from being a space pointer or operating anatomical pointer to a 3D mouse or menu selector. The switch 622 is meant in a generic sense since it does not have to necessarily be physical, but rather could be a mode of phase transition. In any case, the probe can serve both as a pointer and as a function selector on the graphics display. This is important to free the operator from having to push footswitches or from having to have a second person involved in the surgery to change modes. Thus, a portion of this invention relates to the concept of the interface between the operating pointer and the computergraphic display related to switching the pointer from its pointer mode to the 3D mouse mode. In the 3D mouse mode various functionalities can be controlled by the mouse itself on the computergraphic display.

To give specific examples of the embodiment in FIG. 6 with regard to implementations other than the mechanical arm, the case of ultrasonic coupling and optical coupling will be briefly described. In the case of ultrasonic or sonic coupling, points 681 and 682 could be sources of sonic energy. Detectors 671 and 670 could be detectors of sonic energy. By the timing or the amplitude of the received signals by detectors 670 and 671, the processor 618 can determine the orientation of the overall probe 609 by the relative positions of 681 and 682. Alternatively, 670 and 671 may be sources of sonic energy, and 681 and 682 may be receivers. The same statement about triangulation of time-of-light-of signals could apply to give sufficient information to determine the orientation of probe 609 in space, relative to the anatomy of the patient 690. There may be other calibration sources of sonic energy in the field of the patient, possibly either the index points schematically indicated as 612A, 612B, and 612C. In that case, the sonic detectors 670 and 671 could be continually calibrated relative to the field by these calibration or standard sources.

An analogous situation could apply for optical coupling. Element 681 and 682 could be points-like or nearly pointed sources of light and detectors 670 and 671 could be CCD or optical detectors that can determine the position of sources 681 and 682 in their respective fields. These two view fields could thus be calibrated by means of standard or reference lights, such as 612A, 612B, and 612C, so that detectors 670 and 671 are continually calibrated. By this means, the position of the probe or pointer or locator 609 can be determined at all times by this optical detection system. The probe illustrated as a bayonet forceps may be connected by a table which can power the sources 681 and 682, or it can contain batteries which will give self power to these elements, thus becoming a totally mechanically decoupled and electrically decoupled device.

Having described many of the features of the present invention, it is clear that those skilled in the art could make variations of the present described invention and such variations are also claimed in this patent application. The arm can be made of various materials or in various configurations different from those shown in FIG. 1 and 2. The number of joints may be greater than five, although as described above, five is a unique embodiment and has simplifying aspects. Variations on the switching mechanism to toggle the arm from a localizing pointer to a 3D-mouse or other graphic means can be devised. Switching mechanisms other than the foot switch or finger toggle switch may be used and may involve a switch done by a second party remote to the arm. Various configurations of joint geometry may be employed other than the ones shown specifically in the present figures. The localizer geometry and index point structure shown in FIG. 5 based on a dental tray can have wide variations but could serve the same purpose.

What we hereby claim by U.S. Letters Patent are the following:

1. An operating pointer apparatus that can be changed from a pointer mode to a point at patient's anatomy to a computer mouse mode to change the functionality of a computer means, said apparatus comprising:
   (a) an operating pointer adapted to be positioned at said patient's anatomy and to serve as a surgical pointer and which contains position location means which enables a detection means to detect the position of said operating pointer relative to said patient's anatomy;
   (b) an computer with graphics means to display said patient's anatomy based on image data taken of said patient's anatomy and cooperatively connected to said detecting means so as to display the position of said operating pointer relative to said patient's anatomy; and,
   (c) switching means cooperatively associated with said operating pointer, said detecting means, and said computer that enables said operating pointer to be switched from said pointer mode in which the position of said operating pointer is indicated by said computer on said graphics means relative to said patient's anatomy, to said mouse mode in which, when said operating pointer is manipulated by the operator, said operator can change the functional modes as displayed on a functional menu on the graphics means, said functional modes corresponding to the functionality of the operating pointer relative to the computer.

2. The apparatus of claim 1 in which said operating pointer comprises articulating joints and connecting links between said joints and a probe end which is designed to serve as an operating probe to be pointed at said patient's anatomy;
   said position locating means comprising readout means cooperatively connected to said joints and said links to determine their positions in said operating pointer; and,
   said detecting means comprising electronic circuitry that can interpret said readout means and send out information to said computer means.

3. The apparatus of claim 1 wherein:
   said position locating means comprises at least one source of sonic energy; and,
   said detecting means comprises at least two sonic energy detectors which are in two separated spatial positions that can detect the sonic energy emitted by said source of sonic energy, and electronic circuitry to transform said detected energy information into position information of said operating pointer.

4. The apparatus of claim 1 wherein:
said position locating means comprises at least one source of light energy; and,
said detecting means comprises at least two light detectors which are in two separated spatial positions that can detect the light emitted from said light sources, and electronic circuitry to transform said detected light information into positional information of said operating arm.

5. The apparatus of claim 1 wherein said switching means comprises a mechanical switch interposed in the connection between said operating pointer and said computer.

6. The apparatus of claim 1 wherein said switching means comprises software in said computer which detects when the position of said operating pointer has moved away from said patient anatomy by a prescribed amount under which conditions said operating pointer changes automatically from said pointer mode to said mouse mode.

7. An operating arm apparatus having the capability to indicate the position of points in a patient's anatomy and to function alternatively as a pointer and a computer mouse, the operating arm comprising:
(a) articulating joints and connecting linkages between said joints and a tip end which is designed to be positioned at said patient's anatomy and to serve as a surgical pointer;
(b) readout means cooperatively connected to said operating arm to read out the position of said joints and linkages and the tip end of said operating arm;
(c) computergraphics means to display said patient anatomy based on image data taken of said patient's anatomy and adapted to accept said readout means and accordingly to display the relationship of said tip end of said operating arm relative to said patient anatomy; and,
(d) switch means to switch alternately the function of said operating arm from a graphics pointer mode to a mouse mode, wherein in said graphics pointer mode the position of said tip end of said operating arm is indicated on said graphics means, relative to said patient's anatomy, and wherein in said mouse mode the operating arm, when moved in space by the operator, is cooperatively connected by means of said readout means to move a cursor mark displayed on said computer graphics means relative to a functional menu displayed on said computer graphics means, whereby said operator can select from said functional menu by moving said operating arm, and thus select graphics and procedural functions related to said operating arm and said graphics means.

8. The apparatus of claim 7 wherein said switch means is a footswitch control.

9. The apparatus of claim 7 wherein said functional menu includes calibration functions of said operating arm relative to said patient anatomy, and whereby said operator can alternate between said pointer mode and said computer mouse mode to calibrate said operating arm against index points near said patient anatomy by manipulation of said operating arm by itself.

10. The apparatus of claim 7 wherein said operating arm has five joints to provide five angular degrees of freedom for said operating arm's movement.

11. The apparatus of claim 7 in which said tip end can be interchanged with various surgical instruments whereby when said surgical instruments are being used on said patient's anatomy, the position of said surgical instrument can be visualized on said graphic means.

12. The apparatus of claim 7 in which said switching means is enabled by a mechanical switch means.

13. The apparatus of claim 7 in which said switching means is enabled by moving said probe end in space to certain predetermined regions in space relative to the rest of said operating arm.

14. The apparatus of claim 7 in which one of said functional modes on said functional menu is a calibration mode in which said operating arm and said computer can be calibrated at the time of surgery relative to said patient's anatomy by pointing said probe means to known index marks which have been placed on said patient's anatomy and which appear on said image data.

15. The apparatus of claim 14 in which said index marks are connected to a dental impression means which can be positioned and affixed relative to the patient's dentition, said dental impression means being in place during the image process so that said index marks appear in said image data, and said dental impression means being in place at the time of surgery so that said operating arm can be calibrated with respect to said patient's anatomy at the time of surgery.

16. The apparatus of claim 15 in which said index marks comprise at least three non-colinear radiopaque objects attached to said dental impression means that are detectable in said image data.

17. An operating arm apparatus that can be converted from a graphics pointer relative to patient's anatomy to a graphics mouse, said operating arm apparatus consisting:
(a) articulating joints and connecting links between said joints and a probe end which is designed to serve as a surgical probe to be pointed at said patient's anatomy;
(b) interface means cooperatively connected to said operating arm which gives readout on the configuration of said joints and said links;
(c) computer means with graphic display means to display said patient anatomy based on image data taken of said patient's anatomy and adapted to accept said readout means and accordingly to display the relationship of said probe end of said operating arm relative to said patient's anatomy;
said operating arm, interface means, and computer means being so cooperatively adapted that said operating arm can be manipulated by the operator so that it can switch between being said graphics pointer, in which state the position of said probe end is indicated on said graphics display means relative to said patient's anatomy, and being said graphics mouse, in which state when said probe end is moved in space by said operator, a cursor marker is correspondingly moved on said graphics display means relative to a functional menu on said graphics display means and whereby selections can be made by said operator from said functional menu.

18. An operating arm apparatus having the capability to indicate the position of points in a patient's anatomy and to function alternatively as a pointer and a computer mouse, said operating arm comprising:
(a) articulating joints and connecting links between said joints and a probe end which can be held by the operator, and electronic readout of said joints and said links that can interface to a computer; and,
(b) a computer that can store image data of said patient's anatomy and display said image data on graphics display means, and which can accept said electronic readout and can thus indicate the position of said probe relative to said patient's anatomy on said graphics means, and which further enables switching of the state of said operating arm to a computer mouse mode, in which when said probe end is manipulated by said operator, said operator can choose functional modes on a functional menu displayed on said graphics means.

* * * * *